US00PP10731P

United States Patent [19]

Elliott

[11] Patent Number: Plant 10,731

[45] Date of Patent: Dec. 22, 1998

[54] APPLE TREE NAMED 'MT. TIMP GOLD'

[75] Inventor: Grant H. Elliott, Provo, Utah

[73] Assignee: The Burchell Nursery, Inc., Oakdale, Calif.

[21] Appl. No.: 826,654

[22] Filed: Apr. 2, 1997

[51] Int. Cl.[6] ..... A01H 5/00

[52] U.S. Cl. ..... Plt./35.1

[58] Field of Search ..... Plt./34.1, 35.1, Plt./35.2, 35

[56] References Cited

U.S. PATENT DOCUMENTS

| | | | |
|---|---|---|---|
| P.P. 2,835 | 10/1968 | Griffith | Plt./34.1 |
| P.P. 7,209 | 4/1990 | Wick | Plt./35.1 |
| P.P. 9,707 | 11/1996 | Ohrazda et al. | Plt./34.1 |
| P.P. 9,907 | 6/1997 | Hein | Plt./34.1 |

OTHER PUBLICATIONS

GTITM UPOV–ROM Plant Variety Database: Listing for PLP PP 2,835, Oct. 1, 1968, for the variety name 'Blushing Golden'.

*Primary Examiner*—Howard J. Locker
*Attorney, Agent, or Firm*—Wells, St. John, Roberts, Gregory & Matkin, P.S.

[57] ABSTRACT

A new and distinct variety of apple [*Malus domestica*] tree named 'Mt. Timp Gold', which is characterized as to novelty by date of maturity for commercial harvesting and shipment of approximately Sep. 20 through Oct. 10 under the ecological conditions prevailing in the San Joaquin Valley of Central California.

2 Drawing Sheets

BACKGROUND OF THE NEW VARIETY

The present invention relates to a new and distinct variety of apple tree named 'Mt. Timp Gold' and more particularly to an apple tree which bears an attractive predominantly yellow-skinned apple which has a crisp, fine grained texture, and a well balanced flavor.

It has long been recognized that an important factor contributing to the success of any variety of apple tree bearing fruit for the fresh market is its respective date of harvest in relative comparison to other varieties bearing similar fruit in the same season. The variety 'Mt. Timp Gold' is noteworthy, as noted above, in producing an attractively colored fruit which is ripe for harvesting and shipment at approximately the same time in the season as the Red Delicious cultivar, and about 10 days later than the Golden Delicious cultivar under the same ecological conditions prevailing in the San Joaquin Valley of Central California.

ORIGIN AND ASEXUAL REPRODUCTION OF THE NEW VARIETY

The new and distinct variety of apple tree was discovered as a chance seedling growing within the cultivated area of the inventor's property which is located near 4950 North Canyon Road, Provo, Utah, in 1979. The inventor noted the promising characteristics of the chance seedling and in 1986, removed bud wood of the chance seedling and grafted it into test trees growing on the same property. These test trees have been further studied and it has subsequently been determined that the same desirable characteristics observed in the original seedling were expressed in the test trees. Bud wood from these test trees was later removed in 1994 and grafted into test trees growing on the Burchell Nursery, Inc. farm located near Oakdale, Stanislaus County, Calif. The fruit produced from these trees has been compared and contrasted with the fruit produced from the orginal chance seedling and it has been confirmed that this asexual propagation resulted in an apple tree being produced which possesses the same distinctive characteristics as the original chance seedling.

The 'Mt. Timp Gold' apple tree is characterized principally as to novelty by producing an attractively colored fruit which is ripe for harvesting and shipment approximately 20 September through 10 October under the ecological conditions prevailing in the San Joaquin Valley of Central California. This date of harvesting is approximately the same as the Red Delicious cultivar StarkCrimson™ Red Delicious [U.S. Plant Pat. No. 1,565] growing at the same location, and about 10 days later than the Golden Delicious cultivar growing under the same ecological conditions. The present variety is distinguishable from the fruit produced by the Golden Delicious cultivar in that it has a somewhat elongated shape with prominent "typey" calyx end lobes. This is unlike the fruit produced by the Golden Delicious cultivar which has a more rounded calyx end. Further, the present variety has a more yellow colored skin. This is in contrast to the fruit produced by the Golden Delicious which has a skin color which has more green coloration at the time of harvest.

DETAILED DESCRIPTION OF THE DRAWING

The accompanying drawings are color photographs of the present variety.

The first sheet is a photograph of a characteristic twig bearing typical leaves; several leaves showing both the dorsal and ventral coloration thereof; and several mature fruit showing their external coloration sufficiently matured for harvesting and shipment. Additionally, one fruit of the subject variety is dissected in the transverse plane to illustrate the flesh and seed characteristics thereof, all of the subject variety.

The second sheet is a second color photograph of several mature fruit sufficiently matured for harvesting and shipment and showing the skin coloration thereof.

DETAILED DESCRIPTION

Referring more specifically to the pomological details of this new and distinct variety of apple tree, the following has been observed under the ecological conditions prevailing at an orchard which belongs to The Burchell Nursery, Inc. and which is located near Oakdale, Stanislaus County, Calif. All major color code designations are by reference to the "*Directory of Color*" by Maerz & Paul, First Edition, 1930. Common color names are also employed occasionally.

Tree:

*Size.*—Generally — Average as compared to other apple cultivars.

*Productivity.*—Productive.

*Regularity of bearing.*—Regular. The present tree is also considered hardy under the ecological conditions prevailing in the San Joaquin Valley of Central California.

*Vigor.*—Vigorous.

*Figure.*—Upright, to upright spreading in form. The form and density of this tree can be modified by a training system. Presently, the training system used on the subject test trees at the Oakdale, Calif. location is a narrow vase-shaped system. Crotch Angle: variable. Supplemental support was not required for the branches of young trees. Standard vase-shaped pruning was employed for the trees described herein.

*Height.*—The test trees had an average height of approximately 11 feet at the end of the 1996 season.

*Width.*—The original test trees had an average width of 6 feet at the end of the 1996 growing season.

Trunk:

*Thickness.*—Average as compared to other varieties.

*Surface texture.*—Average. The surface texture was not distinctive of the variety.

*Lenticels.*—Numerous lenticels are present. The lenticels are lightly colored and are normally present over the entire surface of the trunk. The lenticels range in size from approximately 2 to about 7 millimeters in length; and from approximately 1 to about 1½ millimeters in height.

*Bark color.*—Generally brown-gray (15-A-7) to a darker gray (8-A-8).

*Graft caliper.*—The subject test trees were high grafted on existing apple stock at a distance of about 75 to 76 cm above the soil. The graft caliper of the three scaffolds arising from this point were approximately 30 to about 38 centimeters.

Branches:

*Size.*—Average, with a relatively smooth surface texture on two-year old or older wood.

*Lenticels.*—Numbers — Numerous small light colored lenticels are usually present.

*Surface texture.*—The shoots of current season growth are highly pubescent. This pubescence is wooly and gray.

*Color.*—Two year old wood — Variable, from gray-brown (15-A-7) to a darker brown (8-J-11). Current season shoots — Pale green (18-H-5); and changing to a reddish brown with advancing senescence, (7-H-9) to approximately (7-J-9). Expanding shoot tips — Pale green (19-G-2).

*Internode length.*—Average. Approximately 15 to about 27 millimeters when measured on young slender shoots.

Leaves:

*Size.*—Generally — Medium to large, when taken from leaves growing on vigorous upright current season's shoots.

*Length.*—Approximately 10.4 to 13.3 centimeters, including the leaf petiole.

*Leaf width.*—Approximately 5.9 to 7.3 centimeters.

*Leaf thickness.*—Average.

*Leaf form.*—Somewhat variable from strongly ovate to approaching oval.

*Leaf tip.*—Form — Acute with the tip apex often twisted sideways.

*Leaf color.*—Upper surface — Variable, dark green. Approximately 23-L-6 to 23-L-9. Lower surface — Gray-green. Approximately 21-H-3 to about 21-J-5.

*Leaf pubescence.*—Upper surface — Lightly pubescent when young, and becoming less so with advancing senescence. Lower surface — Highly pubescent, having a dense, matted, grayish appearance which persists even with advancing senescence.

*Leaf margins.*—Form — Crenate with large slightly irregular crenations. Double crenations may appear on occasion. Shape — Moderately undulate.

*Leaf petiole.*—Size — Average. Length — Approximately 25 millimeters to about 33 millimeters. Thickness — Variable from approximately 1.5 to about 2.5 millimeters when measured at mid-petiole. This measurement often broadens at the base to a width which ranges from approximately 3 to about 6 millimeters. Color — Variable, depending upon the age and light exposure of the leaf. Young leaves normally appear quite pubescent and light green in color (20-I-3). On occasion, the petioles may be slightly tinged with reddish hues. Older leaves, in contrast, appear slightly darker in color (20-J-5) to occasionally green-yellow (19-G-2). Often these older petioles have a red coloration on the base of the petiole (6-K-8). Surface texture — Pubescence is persistent on the petiole surface throughout the entire growing season.

*Leaf stipules.*—Size — Generally, average, and located near the base of the leaf petiole. Form — Normally linear lanceolate. As a general matter, small dark trichomes are often present along the stipule margins. Color — Immature stipules appear pale green in color (19-G-3), and are often tinged with red. Mature stipules have a darker green color, (20-J-6), especially apically. Further, the mature stipules may have a yellowish color which is often tinged with red. This red color normally appears basally. Surface texture — Pubescent. Length — Variable, from approximately 5 to about 9 millimeters. Width — Approximately 1 to about 2.5 millimeters. The stipules normally persist throughout the entire growing season.

Flowers:

*Blooming time.*—Generally — The blooming time is considered to be mid-season to slightly later in relative comparison to other apple cultivars growing in the San Joaquin Valley of Central California.

*Date of full bloom.*—During the 1996 growing season, this was achieved about 10 April.

*Chilling requirement.*—The variety appears to have a low chilling requirement. During the 1995–1996 growing season, the chilling hours were approximately 600 to 620 hours at temperatures at or below 45 degrees Fahrenheit. It was observed that this low accumulation of cold hours substantially extended the bloom period for most apple varieties from about two weeks to a month.

*Flower size.*—Generally — Relatively large.

*Flower diameter.*—At full expansion, the flowers have a diameter of approximately 43 to about 47 millimeters.

*Bloom quantity.*—Generally — Average to abundant.

*Petals.*—Size — Considered large. Length — Approximately 23 to about 28 millimeters. Width — Approximately 18 to about 21 millimeters. Number — 5. Form — Variable. Broadly ovate and occasionally narrowly so.

*Color.*—Immature flowers — White, (1-A-1), to a pale pink (1-B-7).

*Petal color.*—Mature flowers — Variable, from white (1-A-1), to pink (1-C-7). This pink coloration can at times occur in sectors, or occasionally, in streaks within the overall white.

*Petal claw.*—Form — Relatively long, tapered and truncated, especially at the base. Length — Approximately 2.25 to about 3.25 millimeters. Width — Approximately 1 millimeter.

*Petal Margins.*—Form — Relatively smooth and having only slight undulation. As a general matter, the petal margins usually cup inwardly at maturity.

*Petal apex.— Somewhat irregular. Occasionally, the apex appears smooth and slightly domed, and on other occasions, the apex may appear slightly notched.*

*Flower pedicel.*—Surface texture — The surface of the pedicel is considered highly pubescent. Length — Moderately long, approximately 15 to 24 millimeters. Thickness — Approximately 1 millimeter.

*Floral nectaries.*—Color — Pale cream-green (20-H-1).

*Calyx.*—Surface texture — Pubescent. Color — Pale green (20-G-4).

*Sepals.*—Surface texture — Pubescent. Size — Average, and broadly lanceolate and occasionally conic in form. Color — Pale green (20-H-4).

*Anthers.*—Size — Average. Color — Buff-yellow (9-I-2).

*Pollen production.*—Abundant.

*Pollen color.*—Light yellow (10-J-2).

*Filaments.*—Length — Variable, from approximately 7 to about 12 millimeters, and appearing slightly shorter than the pistils at full extension. Color — White (1-A-1), when immature.

*Pistil.*—Length — Approximately 12 to about 14 millimeters. Color— Pale green (20-F-2). Surface texture — Slightly pubescent basally from the ovary to the style division, and on the basal area of the five individual styles just above the style division. The upper portion of the five styles has a slight pubescence although it may from time to time appear glabrous from mid-style to the stigma.

*Bud scales.*—Form — Medium in size and conic in form. Surface Texture — Moderately long and wooly pubescence is present. Color — Brownish-gray (7-E-9). Interior color — Dark brown (8-L-12).

Fruit:

*Maturity when described.*—The present variety of apple is described as it would be found at full commercial maturity under the ecological conditions prevailing at Oakdale, Calif.

*Date of first pick in* 1996.—20 September.

*Date of last pick in* 1996.—10 October.

*Fruit size.—Generally —Medium to large. Uniformity — Uniform.*

*Average cross sectional diameter.*—Approximately 73 to 79 millimeters.

*Average axial diameter.*—Approximately 65 to 77 millimeters.

*Fruit form.*—Generally — Somewhat variable. As a general matter, in the lateral aspect, the fruit is most frequently ovate to conic in form and somewhat elongated. Further, the overall fruit form is somewhat similar to the fruit produced by the Red Delicious cultivar and which is defined in the trade as a "typey". In the apical aspect the fruit is usually globose, but occasionally some fruit may appear oval in shape. In comparison to the Golden Delicious cultivar, the present variety has much more prominent calyx lobes.

*Fruit skin.*—Thickness — Medium, and relatively neutral in flavor. Appearance — Numerous small and inconspicuous dots are present over the fruit skin surface. The dots, vary from stellate to irregular in form. Additionally, some surface russetting is evident. A small amount of surface bloom may be present.

*Fruit skin color.*—Variable, from approximately yellow-green (11-K-1), to a bright yellow-gold (10-L-3). Occasionally, a blushed fruit may be found. When blushed fruit are found, the blush covers about 10% of the fruit's surface area. The blush is a light pink-red color (2-C-10).

*Fruit stem.*—Length — Medium to long — Approximately 19 to about 28 millimeters. Thickness — Approximately 2 to about 2.5 millimeters when measured at mid-stem. The stem appears slightly thicker, or clubbed, at the distal end. Color — Green-tan (13-L-3) to a light brown (13-L-7).

*Stem cavity.*—Width — Average, approximately 28 to 36 millimeters. Shape — The stem cavity shoulder is rounded and the cavity surface at times appears russetted. Depth — Approximately 14 to about 20 millimeters.

*Stem cavity depression.*—Shape — Acute, approaching acuminate.

*Fruit basin.*—The basin of this apple is average in size and relatively wide. The basin shoulders are rounded and usually lobed. Surface texture — Smooth. Occasionally, calyx cracks are evident.

*Calyx.*—Size — Medium. Form — Fully open on some fruit and partially closed on others.

*Calyx lobes.*—Generally — These lobes are persistent on the fruit, and much more prominent than the lobes which appear on the fruit of the Golden Delicious cultivar. Surface texture — Highly pubescent on both the exterior and interior surfaces. The lobes are most frequently separated at the base. The calyx lobes are usually recurved.

*Calyx tubes.*—Shape — Conical in form, often with the floral stamens persistent in the tube. Position — Basal, but approaching median.

*Fruit core.*—Size — Average, and usually median in position within the fruit.

*Core lines.*—Generally — These lines must frequently meet but occasionally a fruit will exhibit lines that approach a clasping in position. Further, the seed cells are closed, or appear only very slightly opened.

*Carpels.*—Form — Obcordate with emarginate outer edges. The surface texture of the outer carpel walls are relatively smooth, and the seeds are free, except for an apical tip attachment. Additionally, the carpel cells are relatively axile and symmetrical when viewed in the horizontal plane.

*Seed count.*—Approximately 6 to about 10.

*Seed.*—Texture — The surface texture is smooth. Color — Dark brown (8-L-9). Shape — The seed apex is acute.

*Flesh color.*—Generally — White (18-A-1) to a very light white-cream (18-B-1). A few long fibers are evident in the flesh varying from white to a very pale green in color (18-B-2).

*Flesh texture.*—Generally — Fine grained, firm, crisp and juicy.

*Fruit flavor.*—The fruit produced by the present variety of apple tree is sweet, and has moderate acidity. Overall, the fruit is well-balanced and pleasant with a distinctly fruity flavor. The variety is also considered superior to the fruit produced by the Golden Delicious apple tree in its complexity and fruitiness. Still further, it is superior to the fruit produced from the Red Delicious cultivar in all aspects of flavor.

*Eating quality.*—Generally — Very good to excellent.

Although the new variety of apple tree herein denominated as 'Mt. Timp Gold' possesses the described characteristics when grown under the ecological conditions prevailing in the San Joaquin Valley of Central California, it is to be understood that variations of the usuall magnitude and characteristics incident to changes in growing conditions, fertilization, pruning, and pest control are to be expected.

Having thus described and illustrated my new variety of apple tree, what is claimed as new and desired to be secured by Letters Patent is:

1. A new and distinct variety of apple tree substantially as illustrated and described and which is somewhat similar in its harvesting date to the Red Delicious cultivar which matures in approximately the same season and about 10 days later than the common commercial variety Golden Delicious but which is distinguished therefrom, and characterized principally as to novelty by producing an attractively colored yellow skinned fruit which is ripe for harvesting and shipment approximately September 20 to about October 10 under the ecological conditions prevailing in the San Joaquin Valley of Central California.

* * * * *

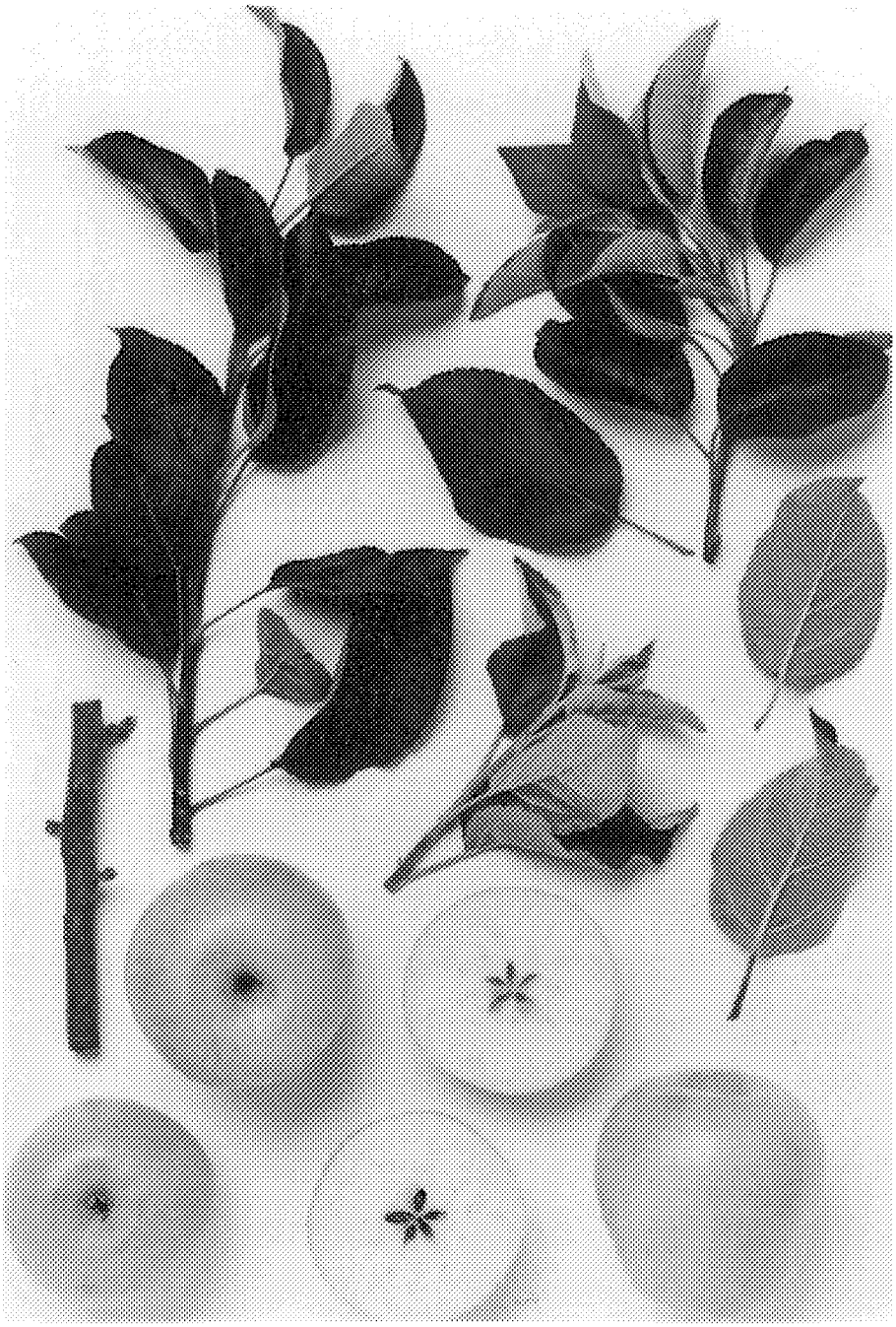

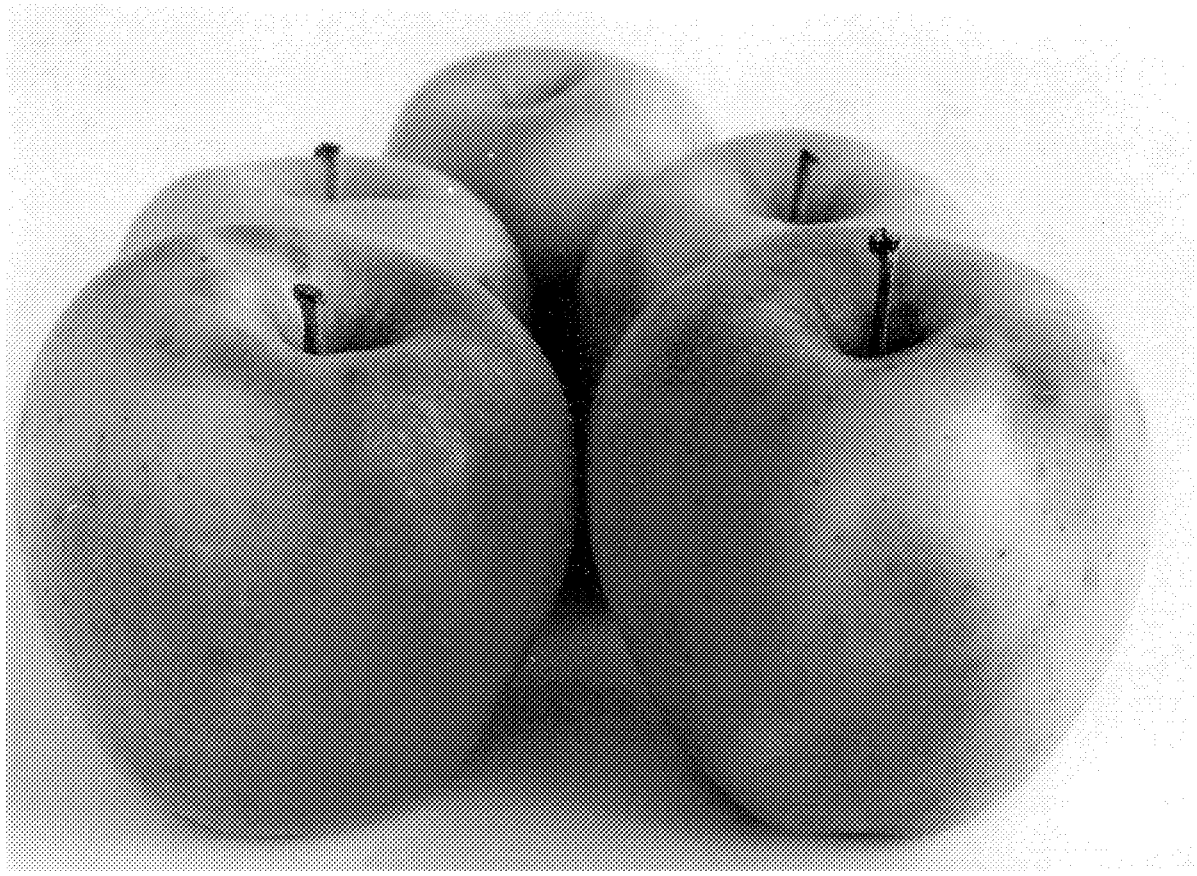

UNITED STATES PATENT AND TRADEMARK OFFICE

CERTIFICATE OF CORRECTION

PATENT NO. : pp -10731

DATED : December 22, 1998

INVENTOR(S) : Grant H. Elliott

It is certified that error appears in the above-identified patent and that said Letters Patent is hereby corrected as shown below:

In column 6, in the paragraph entitled "Core lines", on the first line, delete the word "must" and insert the word --most--

In column 7, in the paragraph entitled "Fruit flavor", on the second line, after the word "sweet", insert the word --spicy,--

Signed and Sealed this

Eleventh Day of May, 1999

*Attest:*

Q. TODD DICKINSON

*Attesting Officer*

*Acting Commissioner of Patents and Trademarks*